United States Patent [19]
Lewis

[11] Patent Number: 5,039,688
[45] Date of Patent: Aug. 13, 1991

[54] METHOD OF PREVENTING AIDS TRANSMISSION RESULTING FROM BLOOD TRANSFUSIONS

[75] Inventor: Peter J. Lewis, London, England

[73] Assignee: Merrell Dow Pharmaceuticals, Inc., Cincinnati, Ohio

[21] Appl. No.: 338,798

[22] Filed: Apr. 14, 1989

[30] Foreign Application Priority Data

Apr. 19, 1988 [GB] United Kingdom ................. 8809177

[51] Int. Cl.$^5$ ...................... A61K 31/44; A61K 31/14
[52] U.S. Cl. .................................. 514/358; 514/643; 514/885; 604/4; 604/7
[58] Field of Search ....................... 514/358, 643, 885; 604/4, 7

[56] References Cited

PUBLICATIONS

Gallo and Montagnier, Scientific American, vol. 259, No. 4, 1988, pp. 41–48.
Rey et al, Biochemical and Biophysical Research Communications, vol. 121, No. 1, 1984, pp. 126-133.
W. E. Gutteridge, British Medical Bulletin, vol. 41, No. 2, 162-168 (1985).
Z. Brener, Pharmac. Ther. 7, pp. 71-90 (1979).
Pharmaceutical Industry and Healthcare News Database.
Chemical Business News Database.

Primary Examiner—Cecilia Shen
Attorney, Agent, or Firm—Stephen L. Nesbitt

[57] ABSTRACT

Quaternary ammonium salts such as the benzalkonium chlorides and cetylpyridinium chloride can prevent the transmission of AIDS-causing virus through blood transfusions and through the use of blood products prepared using the blood of an AIDS infected individual.

3 Claims, No Drawings

METHOD OF PREVENTING AIDS TRANSMISSION RESULTING FROM BLOOD TRANSFUSIONS

This invention relates to the prevention of the transmission of AIDS-causing virus through blood transfusions and through the use of blood products where the blood donor is infected with an AIDS-causing virus.

BACKGROUND OF THE INVENTION

A great deal of research is currently underway to develop treatments and cures for viral infections in humans and in animals. Notably the incidence of AIDS and ARC in humans is increasing at an alarming rate. The five year survival rate for those with AIDS is dispiriting and AIDS patients, whose immune systems have been seriously impaired by the infection, suffer from numerous opportunistic infections including Kaposi's sarcoma and *Pneumocystis carninii* pneumonia. No cure is known and current treatments are largely without adequate proof of efficacy and have numerous untoward side effects. Fear of the disease has resulted in social ostracism of and discrimination against those having or suspected of having the disease.

A significant problem in preventing the spread of AIDS is that the disease can be transferred from an infected individual by way of a blood transfusion or through the use of blood products, such as the coagulation factor VIII used by many hemophiliacs and such as blood serum and blood plasma, using blood donated from an individual infected with an AIDS-causing virus. The problem is confounded because intravenous drug users, who as a class have a high incidence of AIDS, are also quite likely to be blood donors. While an effective test has been developed which detects HIV-1 virus in blood donated for transfusions, some transmission of disease still occurs through blood tranfusions. For example, some individuals are highly infectious for up to six months before the test will indicate presence of AIDS-causing virus in the blood of such individuals. Moreover, a second AIDS-causing virus, HIV-2, is not detected by the present blood test. While the risk of contracting AIDS from transfusion is quite low because testing has become routine, it would be highly desirable to further reduce the risk of transmission of AIDS-causing virus resulting from blood transfusions.

The quaternary ammonium salts have long been known to possess topical antiseptic and disinfectant properties. For example, cetylpyridium chloride has long been known to posssess antimicrobial activity and has been used in mouthwashes and as a topical antiseptic and as a disinfectant for many years. The benzalkonium chlorides are widely used in disinfectant products. The quaternary ammonium salts are known to be quite effective against gram positive bacteria and to a lesser extent are effective against the gram negative bacteria. These salts, in particular, the benzalkonium chlorides, are not known to be significantly anti-viral. Only recently has the anti-AIDS virus activity of the benzalkonium chlorides been recognized when employed in a contraceptive cream.

While crystal blue, an antiseptic dye, has been used for many years in tropical countries to prevent the transmission by blood transfusion of various parasitic diseases such as African trypanosomiasis and Chagas' disease, the use of this and other quaternary ammonium salts to prevent disease transmission by blood transfusion has not been actively pursued despite the overwhelming need for such prophylactic therapy. Surprisingly, it has now been found that the quaternary ammonium salts, in particular cetylpyridinium chloride, can inactivate AIDS-causing virus in donated whole blood intended for use in blood transfusions and in the preparation of other blood products. Such finding is all the more surprising because the benzalkonium chlorides and to some extent cetylpyridium chloride as well as all the other quaternary ammonium salts are known to be deactivated by contact with living tissue and thus the quaternary ammonium salts have been used only topically. Applicant's unexpected discovery should prove most useful in the prevention of the transmission of this insidious disease.

DETAILED DESCRIPTION OF THE INVENTION

The term "quaternary ammonium salt" as used herein is intended to mean the class of organic compounds in which a positively charged nitrogen atom shares its valence electrons with carbon atoms which are part of organic groups. The quaternary ammonium salts of this invention can have from one to four alkyl groups attached to the positively charged nitrogen atom or the positively charged nitrogen atom can be part of a saturated or unsaturated ring system. An alkyl group of this invention can be a straight, branched, or cyclic alkyl group, can have from 1 to about 20 carbon atoms, and can have from one to four olefinic or acetylenic unsaturations. Examples of suitable alkyl groups are methyl, ethyl, n-propyl, n-butyl, cyclohexyl, n-octyl, decyl, dodecyl, nonadecyl, didecyl, 3,7-dimethyloctyl, 3,7,11-trimethyl-2,6,10-octatrienyl, 8,11,14-heptadecatrienyl, 3,7-dimethyl-6-octenyl, 9-undecenyl, 2-heptynoyl, 9-decynyl, 8-heptadecynyl, cyclopentylmethyl, and cetyl. Preferably at least one of the alkyl groups will have from 12 to 20 carbon atoms and any other alkyl groups, if present, will be substantially lower such as those alkyl groups having from one to four carbon atoms, and will be preferably methyl or ethyl. More preferably the higher alkyl group will be a straight chain alkyl group of from 12 to 18 carbon atoms. Examples of positively charged nitrogen atoms which are part of a saturated or unsaturated ring system are pyridinium and quinolinium groups.

Typically quaternary ammonium salts are prepared by reacting a tertiary amine with an alkyl halide. Whether prepared from such a tertiary amine or not, quaternary ammonium salts of this invention can be conceptually thought of as derived from tertiary amines of the classes a) dimethylalkylamines, b) diethoxylated monoalkyqlamines, c) methyldialkylamines, d) ethoxylated dialkylamines, e) propoxylated monoalkylamines, f) ethoxylated fatty amidoamines, g) imidazolines, h) benzyldialkylamines, i) quinolines, or j) pyridines.

The anionic counterion of the quaternary ammonium salts of this invention can be any pharmaceutically acceptable anion generally used in pharmaceutical agents. Typically the anionic counterion will be a halide ion. The halide ion can be a fluoride, chloride, bromide, or iodide with bromide and chloride being preferred. Chloride is most preferred. While the halide salts are preferred, other salts are included within the scope of this invention such as hydroxides, sulfates, nitrates, fumarates, benzoates, ascorbates, acetates, tartrates, citrates, and malates.

Preferred quaternary ammonium salts used in this invention are the dimethylalkylbenzalkonium halides, particularly the benzalkonium chlorides especially wherein the alkyl group is of from 12 to 16 carbon atoms. The benzalkonium chlorides are a well known class of quaternary ammonium salts and are a mixture of alkyl dimethylbenzylammonium chlorides wherein the alkyl group is a mixture of alkyl groups of from about 8 to about 18 carbon atoms. Also preferred are the alkylpyridinium halides, particularly the alkylpyridinium chlorides, especially wherein the alkyl group is from 16 to 18 carbon atoms. Cetylpyridinium chloride is the most preferred quaternary ammonium salt for use in the method of this invention.

Quaternary ammonium salts when added to donated blood intended for transfusions or intended for the preparation of other blood products can prevent the transmission of AIDS-causing viruses. The ability of the quaternary ammonium salts to prevent retroviral transmission can be shown by the procedure described by M. A. Ray, et al., in Biochemical and Biophysical Research Communications, volume 121(1), pages 126-133 (1984). In this procedure a crude viral pellet is obtained from cell free supernatant of HIV-1 producing CEM line and suspended to obtain a standard inoculum of reverse transcriptase activity of $1.6 \times 10^6$ cpm/ml. Cetyl pyridinium chloride was added to aliquots at concentrations of 0.03 up to 10 g/l and for different contact times at 37° centigrade. Antiviral activity was measured by reverse transcriptase assay and by infectivity for PHA stimulated human T lymphocytes in culture. Cetylpyridinium chloride inhibits HIV 1 infectivity on T lymphocytes at 10 mg/l after only 10 minutes. There was no change in reverse transcriptase activity.

Ideally the quaternary ammonium salts are added to the donated whole blood immediately after donation but can be added any time before the blood is used in transfusion or before the whole blood is used in the preparation of blood products so long as sufficient time is allowed for the salt to inactivate the AIDS-causing virus. While higher concentrations of added quaternary ammonium salts will cause more rapid inactivation of AIDS-causing virus in the donated blood, longer incubation times will permit the use of lower concentrations of quaternary ammonium salts. Generally the least amount of added quaternary ammonium salt which will cause complete loss of infectivity of the AIDS-causing virus in blood is preferred, because even though the quaternary ammonium salts are not highly toxic, all such salts are detrimental to living tissue at sufficiently high concentration. For example, cetylpyridinium chloride at a concentration in the blood of 0.03 g/l would be expected to cause some toxic effects in the patient receiving the blood if the patient receives more than about 3 or 4 international units of blood so treated. Ideally the concentration of quaternary ammonium salt will be chosen so that the donated blood will be free of AIDS-causing virus and available for use in transfusions or for use in the preparation of blood products after about 1 or 2 hours. For cetylpyridinium chloride this amount can be from about 0.03 to about 10 g per liter of blood. The quaternary ammonium salts will generally be added as a solution to the blood and the solution concentration will be chosen so that an effective amount of quaternary ammonium salt in the donated blood will be an amount effective to inactivate any AIDS-causing virus in about 1 to 2 hours yet not cause substantial dilution of the blood by the solvent. Water is a preferred solvent for the quaternary ammonium salts used in this invention and isotonic solutions of the quaternary ammonium salt in water are most preferred. As an example of a composition useful in carrying out the method of this invention, 0.03 g of cetylpyridinium chloride can be dissolved in 1 ml of lactated Ringer's solution and the resulting solution added to donated whole blood. After about 1 to 2 hours the blood is AIDS-causing virus free.

I claim:

1. A method for preventing the transmission of AIDS-causing virus by blood transfusion or by the use of blood products which comprises adding an effective amount of a quaternary ammonium salt selected from the group consisting of benzalkonium chloride and cetylpyridium chloride to the whole donated blood prior to transfusion of the blood to a receiving patient or before use of the donated blood in the preparation of blood products.

2. A method of claim 1 wherein the quarternary ammonium salt is benzalkonium chloride.

3. A method of claim 1 wherein the quarternary ammonium salt is cetylpyridium chloride.

* * * * *